United States Patent
Sunagawa et al.

(10) Patent No.: US 6,770,034 B2
(45) Date of Patent: Aug. 3, 2004

(54) ULTRASONIC DIAGNOSTIC APPARATUS

(75) Inventors: Kazuhiro Sunagawa, Sendai (JP); Yoshinao Tannaka, Aiko-Gun (JP); Hiroshi Kanai, Sendai (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/174,979

(22) Filed: Jun. 20, 2002

(65) Prior Publication Data

US 2003/0009101 A1 Jan. 9, 2003

(30) Foreign Application Priority Data

Jul. 2, 2001 (JP) ........................... 2001-200574

(51) Int. Cl.[7] ................................. A61B 8/00
(52) U.S. Cl. ................ 600/443; 600/437; 600/438; 600/454; 600/465
(58) Field of Search ............................ 600/437, 438, 600/441, 442, 443, 453, 454, 465, 468

(56) References Cited

U.S. PATENT DOCUMENTS

| | | | |
|---|---|---|---|
| 4,334,543 A | | 6/1982 | Fehr |
| 4,583,552 A | | 4/1986 | Iinuma |
| 4,790,321 A | * | 12/1988 | Miwa et al. ............... 600/443 |
| 5,107,840 A | * | 4/1992 | Bonnefous ................ 600/454 |
| 5,246,006 A | | 9/1993 | Kanda et al. |
| 5,329,929 A | | 7/1994 | Sato et al. |
| 5,522,392 A | | 6/1996 | Suorsa et al. |
| 5,615,680 A | * | 4/1997 | Sano ....................... 600/437 |
| 5,820,561 A | * | 10/1998 | Olstad et al. ............. 600/453 |
| 5,938,611 A | * | 8/1999 | Muzilla et al. ............ 600/455 |
| 6,099,471 A | * | 8/2000 | Torp et al. ................ 600/438 |
| 6,132,380 A | * | 10/2000 | Cohen et al. ............. 600/481 |
| 6,155,980 A | * | 12/2000 | Chiao et al. .............. 600/447 |
| 6,258,031 B1 | * | 7/2001 | Sunagawa et al. ........ 600/443 |
| 6,270,459 B1 | * | 8/2001 | Konofagou et al. ....... 600/449 |
| 6,520,915 B1 | * | 2/2003 | Lin et al. .................. 600/453 |

FOREIGN PATENT DOCUMENTS

| | | |
|---|---|---|
| EP | 1 079 242 | 2/2001 |
| JP | 10-5226 | 1/1998 |

* cited by examiner

*Primary Examiner*—Dennis W. Ruhl
*Assistant Examiner*—William C. Jung
(74) *Attorney, Agent, or Firm*—Wenderoth, Lind & Ponack, L.L.P.

(57) ABSTRACT

The present invention provides an ultrasonic diagnostic apparatus. The ultrasonic diagnostic apparatus comprises an ultrasonic probe (1) for transmitting ultrasonic pulses into a living body and receiving ultrasonic reflected waves from the living body, a phase-detecting section (5) for detecting each phase of the ultrasonic reflected waves, and a phase-difference detecting section (6) for determining a phase difference in the repetition period of the ultrasonic transmitting/receiving operation according to the detected phase signals. The ultrasonic diagnostic apparatus further includes a data analyzing section (7) for calculating the movement velocity of the living body tissue and the blood flow velocity according to the phase difference of the ultrasonic reflected waves and tracking the movements of the living body tissue and the blood according to the movement values calculated by the velocities, and a display section (13) for displaying the tracked results and the movement value and velocity waveform of the living body tissue and the blood simultaneously through a display control section (10).

27 Claims, 8 Drawing Sheets

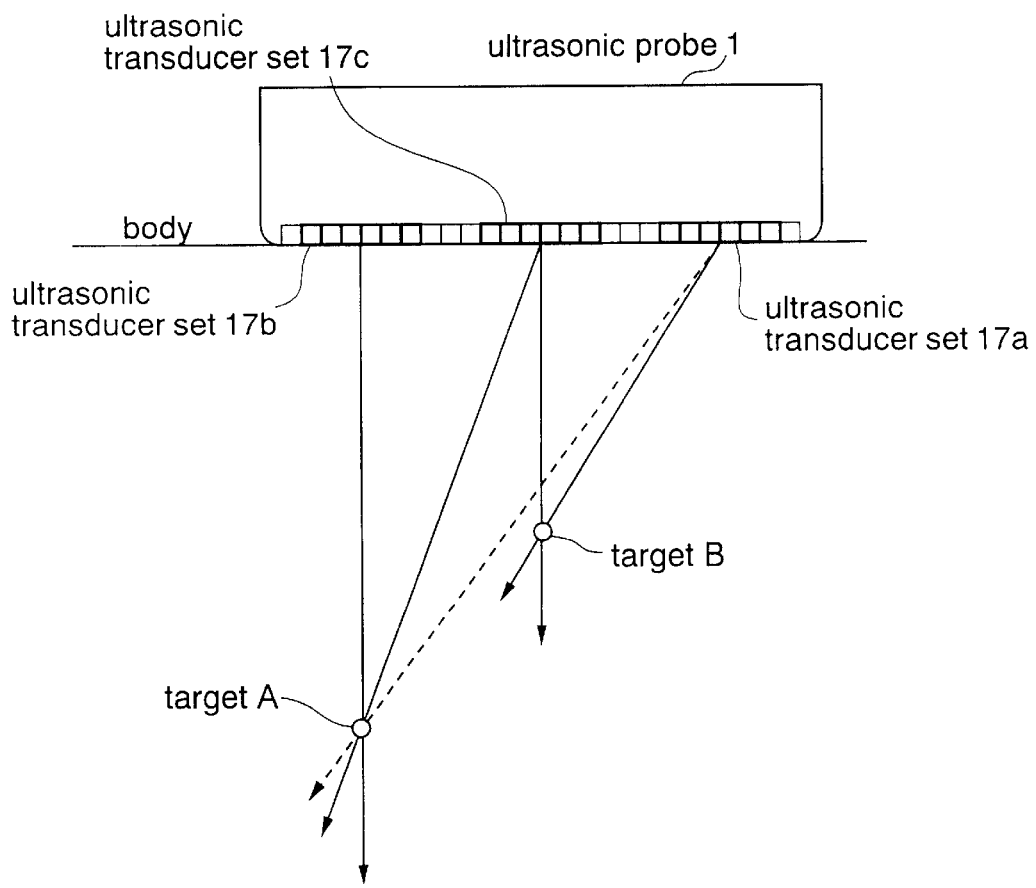
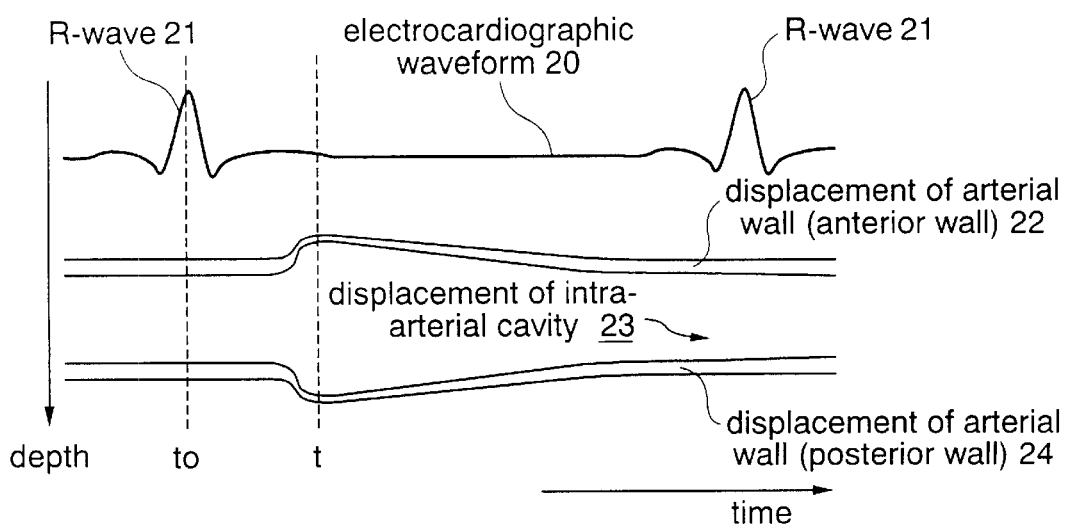

ULTRASONIC DIAGNOSTIC APPARATUS

FIELD OF THE INVENTION

The present invention relates to an ultrasonic diagnostic apparatus for transmitting ultrasonic waves to a tissue in a living body, detecting the phases of ultrasonic echo signals reflected from the living body by using phase detecting means to calculate tissue movement or blood flow velocity in the living body according to the detected phases, and displaying the calculated result.

BACKGROUND OF THE INVENTION

A conventional ultrasonic diagnostic apparatus has various functions, such as a B-mode function for displaying tomographic images of a tissue in a living body, an M-mode function for displaying a temporal variation of the movement of a tissue in a living body, an FFT Doppler mode function for displaying a temporal variation of blood flow velocity, and a color Doppler mode function for displaying the moving state of a moving region in a living body, such as blood flow, by coloring the moving region according to its moving direction.

In those instances where such a conventional ultrasonic diagnostic apparatus is used to diagnose carotid arteries for the purpose of an arteriosclerosis diagnosis, the characteristic of a lesion is determined by using the B-mode function to evaluate the inner diameter of a blood vessel and the thickness of the blood vessel wall; using brightness in a tomographic image from the B-mode imaging to evaluate a raised lesion resulting from thrombus adhesively accumulated on the blood vessel wall; using the M-mode function to evaluate the temporal variation of the inner diameter of the blood vessel in response to a heartbeat; and using the FFT Doppler function or the color Doppler function to evaluate the blood flow velocity in the stenotic region of the blood vessel due to the raised lesion.

Further, Japanese Patent Laid-Open Publication No. Hei 9-323485 discloses a Tissue Doppler Imaging technique to measure the movement of a tissue in a living body. This technique is directed to grasp the movement of a tissue in a living body quantitatively by imaging a target region with color according to the magnitude and/or direction of the tissue movement.

When diagnosing carotid arteries for the purpose of the arteriosclerosis diagnosis, it is necessary to grasp easily the relationship between blood flow variation and arterial wall movement in order to evaluate an influence of a raised lesion arising in the carotid arteries.

However, when the aforementioned conventional ultrasonic diagnostic apparatus is used to diagnose a raised lesion mainly arising from thrombus, the obtained tomographic image of the raised lesion is displayed with low brightness due to properties of the tissue of the raised lesion. Thus, in the evaluation method using the B-mode function, there is a problem that it is difficult to discover such a lesion, and it is impossible to quantitatively evaluate the characteristic of the lesion according to brightness in the obtained tomographic image.

In the conventional ultrasonic diagnostic apparatus additionally employing the color Doppler function, even if a lesion has a low brightness which is difficult to discover through the B-mode function, the lesion can be colored to distinguish it from lumen having a blood flowing therethrough, thereby providing higher diagnostic accuracy than that obtained by using only the B-mode function. However, it is difficult to quantitatively grasp the arterial wall movement in relation to the blood pressure and/or blood flow variation.

In addition, for achieving the color Doppler function, it is essential to perform a given processing for accurately distinguishing blood flow (fast movement) from body movement (slow movement) to pick up information related only to the blood flow. As a result, signals representing the amount of the slow movement from the living body are filtered out, and thereby the tissue movement and blood flow variation in the living body cannot be measured simultaneously.

Even though the quantitative ascertainment of the tissue movement can be achieved by additionally employing the tissue Doppler imaging, it is still difficult to ascertain the arterial wall movement in relation to the blood pressure and/or blood flow variation.

SUMMARY OF THE INVENTION

The present invention is directed to solve the aforementioned problems in the conventional apparatus. It is, therefore, an object of the present invention to provide an improved ultrasonic diagnostic apparatus capable of simultaneously measuring the movement velocity and displacement of a tissue in a living body, such as blood flow or arterial wall, particularly for diagnosing lesions in the circulatory system, so that a display can be obtained in which the relationship between the blood flow variation and the arterial wall movement can be easily obtained.

In order to achieve the above object, the present invention provides an ultrasonic diagnostic apparatus comprising ultrasonic transmitting/receiving means for transmitting ultrasonic pulses into a living body and receiving ultrasonic reflected waves reflected from the living body through an ultrasonic probe; phase detecting means for detecting each phase of the ultrasonic reflected waves received by the ultrasonic transmitting/receiving means; phase-difference detecting means for detecting a phase-difference between a plurality of phase signals detected continuously by the phase detecting means; data analyzing means for analyzing a movement of a tissue including a blood flow in the living body according to the detected phase difference; and display means for displaying the movement of the living body tissue. Because of this construction, it is possible to analyze the movement of the living body tissue through a simplified method of detecting the phase-difference between the received ultrasonic signals.

In the above ultrasonic diagnostic apparatus of the present invention, the ultrasonic probe may include a plurality of ultrasonic transducers. In this case, the ultrasonic diagnostic apparatus further includes delay control means for controlling each delay value of the ultrasonic pulses and ultrasonic reflected waves which are transmitted and received by each of the plurality of ultrasonic transducers to control each deflection angle of acoustic lines defined by the ultrasonic pulses and the ultrasonic reflected waves. Further, the phase detecting means is adapted to detect the phase-difference for each of the plurality of acoustic lines having different deflection angles, and the data analyzing means is adapted to calculate the movement velocity and displacement of the living body tissue according to the phase-difference for each of the plurality of acoustic lines. Because of this construction, it is possible to calculate the movement velocity and displacement of the living body tissue with a high degree of accuracy through a simplified method of detecting the phase-difference of ultrasonic received signals for each of the plurality of acoustic lines having different distortion angles.

In the above ultrasonic diagnostic apparatus of the present invention, the data analyzing means may be adapted to detect the orthogonal and parallel components of the movement velocity of the living body tissue according to the phase-difference for each of the plurality of acoustic lines. And the data analyzing means may be adapted to calculate the movement velocity and displacement of the living body tissue according to the detected orthogonal and parallel components of the movement velocity. In this case, the orthogonal and parallel components are orthogonal to and parallel to the surface of the ultrasonic probe, respectively. Because of this construction, it is possible to provide enhanced accuracy in the calculation of the movement velocity and displacement of the living body tissue based on the detection of the phase-difference of ultrasonic received signals.

The ultrasonic diagnostic apparatus according to the present invention may further include transducer selecting means for selecting the plurality of ultrasonic transducers. The transducer selecting means is adapted to form a plurality of ultrasonic transducer sets each composed of a given number of adjacent ultrasonic transducers selected from the plurality of ultrasonic transducers, and to select a plurality of the ultrasonic transducer sets. In this case, the data analyzing means is adapted to calculate the movement velocity and displacement of the living body tissue according to the phase-difference for each of the acoustic lines of the selected ultrasonic transducer sets. Because of this construction, it is possible to deflect the acoustic line easily, and it is possible to detect phases from a plurality of acoustic lines so as to calculate the movement velocity and displacement of the living body tissue accurately.

In the above ultrasonic diagnostic apparatus of the present invention, the delay control means may be adapted to arbitrarily control each deflection angle of the acoustic lines of the ultrasonic transducer sets. In this case, the data analyzing means is adapted to calculate the movement velocity and displacement of the living body tissue according to the phase-difference for each of the acoustic lines. Because of this construction, it is possible to change the deflection angle of the acoustic line easily, so as to provide enhanced flexibility in calculating the movement velocity and displacement of the living body tissue.

The ultrasonic diagnostic apparatus of the present invention may further include diagnostic-image construction means for constructing an ultrasonic diagnostic image according to information related to the ultrasonic reflected waves. The ultrasonic diagnostic image may have a plurality of measurement regions. And at least one of the measurement regions can be selected from the ultrasonic diagnostic image constructed by the diagnostic image construction means. In this case, the phase-difference detecting means is adapted to detect the phase-difference of the ultrasonic reflected waves associated with the at least one of selected measurement region simultaneously or almost simultaneously, so as to allow the data analyzing means to calculate the movement velocity and displacement of the living body tissue in the selected measurement region. Because of this construction, it is possible to calculate the movement velocity and displacement of the target region while checking the target region by the ultrasonic diagnostic image, so that accuracy in diagnosis is improved.

In the above ultrasonic diagnostic apparatus of the present invention, it is possible to select at least one of any measurement region from the ultrasonic diagnostic image constructed by the diagnostic image construction means. The delay control means may be adapted to set each deflection angle of the acoustic lines for each of scan frames, and the phase-difference detecting means is adapted to detect the phase-difference of the ultrasonic reflected waves for each of the scan frames having an arbitrarily-set deflection angle, simultaneously or almost simultaneously, in the at least one of selected measurement regions. Because of this construction, it is possible to calculate the movement velocity and displacement of the target region without degrading the image quality of the ultrasonic diagnostic image.

The ultrasonic diagnostic apparatus of the present invention may further include means for converting the movement velocity and displacement in the living body tissue to polar coordinate system to determine velocity value and angle. Because of this construction, it is possible to provide enhanced accuracy in the calculation of the movement velocity and displacement of the living body tissue.

The ultrasonic diagnostic apparatus of the present invention may further include electrocardiographic-signal input means for inputting a signal from an electrocardiograph, and means for displaying an image on the display means to provide the relationship between the input electrocardiographic signal and the displacement of an arterial wall. Because of this structure, it is possible to simultaneously display the displacement of the living body tissue and the electrocardiographic waveform. Thus, it is particularly effective in a diagnosis of the circulatory system.

In the above ultrasonic diagnostic apparatus of the present invention, the data analyzing means may be adapted to calculate the movement velocity and displacement of each of an arterial wall and an intra-arterial blood flow, and to determine the relationship between the movement velocity or displacement of the arterial wall and the movement velocity or displacement of the intra-arterial blood flow, so as to allow the display means to display a graph representing the relationship. Because of this construction, it is possible to provide the graph representing the relationship between the movement velocity or displacement of the arterial wall and the movement velocity or displacement of the intra-arterial blood flow. Thus, it is possible to ascertain the state of the lesion in the diagnostic region.

Further, in the above ultrasonic diagnostic apparatus of the present invention, the data analyzing means may be adapted to arbitrarily set a delay time from the time when an R-wave of the electrocardiographic signal is generated, and to calculate the movement velocity and displacement of each of an arterial wall and an intra-arterial blood flow at the set delay time, so as to allow the display means to display a graph representing the relationship between the movement velocity or displacement of the arterial wall and the movement velocity or displacement of the intra-arterial blood flow. Because of this construction, it is possible to provide the graph representing the relationship between the movement velocity or displacement of the arterial wall and the movement velocity or displacement of the intra-arterial blood flow in conjunction with a heartbeat. Thus, it is possible to ascertain the relationship between the lesion and the heartbeat.

The ultrasonic diagnostic apparatus of the present invention may further include blood-pressure input means for inputting a signal from a blood-pressure meter. In this case, the data analyzing means is adapted to normalize the displacement of an intra-arterial blood flow with a maximum blood pressure and a minimum blood pressure entered from the blood-pressure meter to convert the displacement into a blood pressure variation so as to allow the display means to display a graph representing the relationship between the movement velocity or displacement of the arterial wall and the blood pressure variation. Because of this construction, it is possible to provide the graph representing the relationship between the movement velocity or displacement of the arterial wall and the blood pressure variation so as to ascertain the relationship between the blood pressure variation and the arterial wall.

BRIEF DESCRIPTION OF THE DRAWINGS

FIG. 7 is an explanatory diagram of a movement velocity measurement of a plurality of targets to be measured according to the third embodiment of the present invention;

FIG. 8 illustrates an electrocardiographic waveform and the displacement of an arterial wall according to a fifth embodiment of the present invention.

Figure 1:
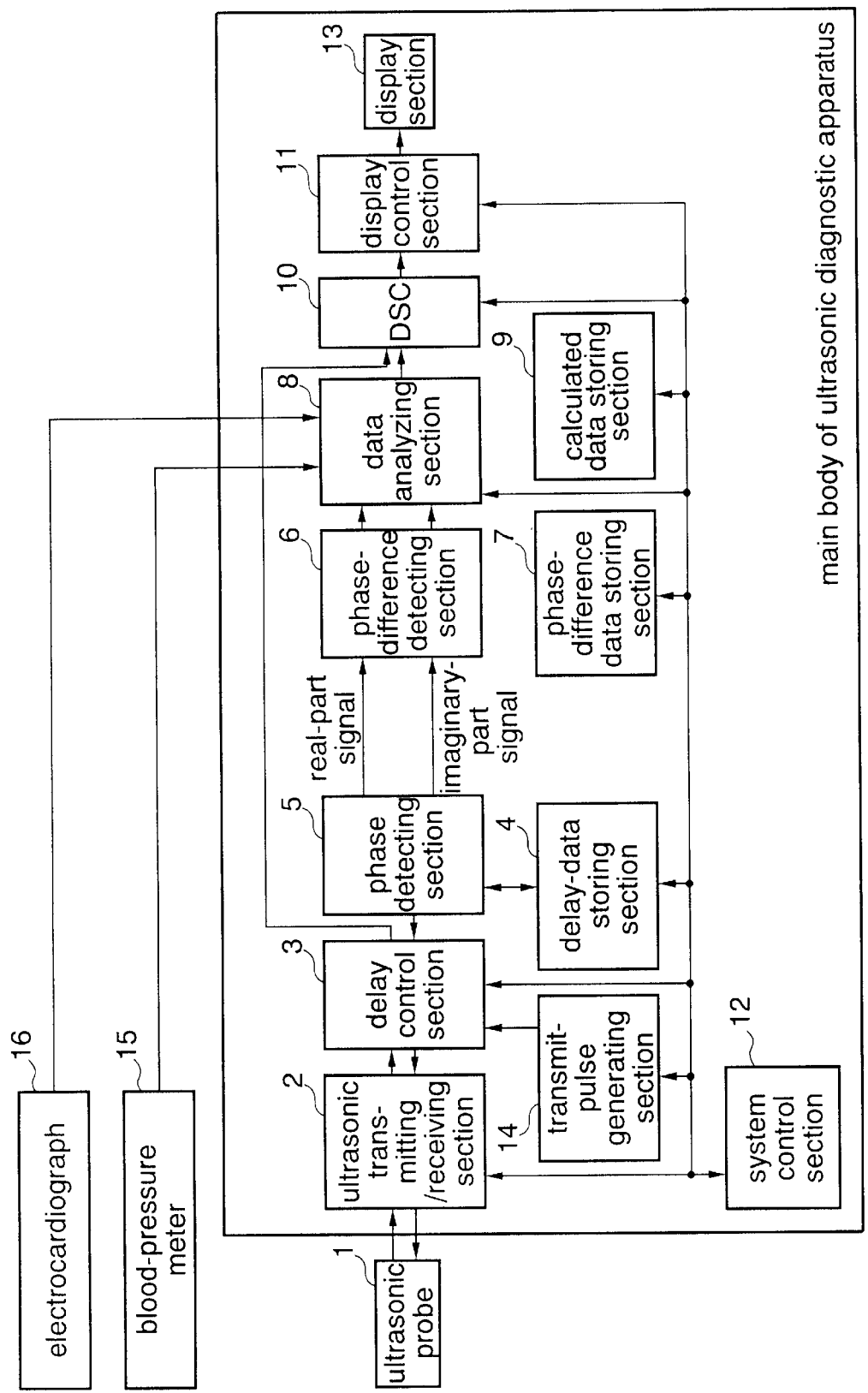
FIG. 1 is a block diagram of an ultrasonic diagnostic apparatus according to a first embodiment of the present invention.

DESCRIPTION OF THE PREFERRED EMBODIMENT (First Embodiment)

With reference to the drawings, a first embodiment of the present invention will be described.

The construction of an ultrasonic diagnostic apparatus according to the first embodiment of the present invention will now be described. An ultrasonic probe 1 includes a plurality of ultrasonic transducers, each of which transmits an ultrasonic transmission pulse to a living body at predetermined time-intervals and receives a resulting ultrasonic reflected wave from a tissue of the living body at predetermined time-intervals. A transmit-pulse generating section 14 generates ultrasonic transmission pulses to be transmitted by the ultrasonic probe 1. An ultrasonic transmitting/receiving section 2 amplifies each of the ultrasonic pulses to be transmitted by each of the ultrasonic transducers of the ultrasonic probe 1. The ultrasonic transmitting/receiving section 2 also processes each of the ultrasonic reflected waves received by each of the ultrasonic transducers of the ultrasonic probe 1, and then outputs the received ultrasonic reflected waves to a phase detecting section 5 as an ultrasonic received signal. A system control section 12, serving as a transducer selecting means, controls to select desired ultrasonic transducers from the plurality of ultrasonic transducers. A delay control section 3 controls each delay time of the ultrasonic transmission pulses and the ultrasonic received signals which are transmitted and received by each of the plurality of ultrasonic transducers to control each deflection angle of the direction for the ultrasonic transmitting/receiving operation (directions of acoustic lines). The delay-controlled ultrasonic received signal is outputted to a digital scan converter (DSC) 10 to provide a B-mode display or a tomographic image and a M-mode display for displaying the temporal variation of a displacement value of the tissue. The delay-controlled ultrasonic received signal is also outputted to the phase detecting section 5 to detect a phase difference and calculate the movement velocity of a target to be measured. A delay-data storing section 4 stores data of respective delay times of the ultrasonic transducers. The stored delay data are determined in consideration of a predetermined deflection angle of the acoustic line for each of the ultrasonic transmitting/receiving operation to control the ultrasonic transducers by the delay control section 3. The delay control section 3 reads out the different delay data corresponding to each of the ultrasonic transmit pulses to allow each of the ultrasonic transmit pulses to be transmitted and received at a different deflection angle.

The phase detecting section 5 detects each phase of the ultrasonic received signals, each of which is provided with a predetermined delay time at the delay control section 3, and divides it into a real-part signal and an imaginary-part signal. A phase-difference detecting section 6 detects a phase difference between the plurality of ultrasonic received signals received at the predetermined intervals, or between the plurality of ultrasonic received signals in one image (in a plurality of scan frames) to be displayed on a display section 13, according to the real-part signal and the imaginary-part signal outputted from the phase detecting section 5. A phase-difference data storing section 7 temporarily stores the phase data for each of the plurality of the ultrasonic transmission pulses which are detected at the phase-difference detecting section 6 and are received at the predetermined intervals. The phase-difference detecting section 6 uses the stored phase data to compare the phase data of the ultrasonic received signal previously received and stored in the phase-difference data storing section with the phase data of the currently received ultrasonic received signal, and detects a phase difference between the plurality of ultrasonic transmission pulses received at the predetermined intervals or a phase difference between the plurality of scan frames. A data analyzing section 8 calculates the movement velocity and displacement of the target living body tissue according to the phase difference detected by the phase-difference detecting section 6. A blood-pressure meter 15 and an electrocardiograph 16 each connected to the ultrasonic diagnostic apparatus output a maximum and minimum blood pressure values and an electrocardiographic waveform to the data analyzing section 8, respectively. The data analyzing section 8 uses these input signals to detect the timing of a heartbeat and ascertain a blood pressure variation in conjunction with the heartbeat. A calculated data storing section 9 stores data for the data analyzing section 8 to calculate the movement velocity and the displacement of the living body tissue.

The DSC 10 constructs an ultrasonic diagnostic image according to the ultrasonic received signals for the B-mode and M-mode displays inputted from the delay control section 3. Further, each of the scan directions of this ultrasonic diagnostic image and the information related to the movement velocity and the displacement of the living body tissue inputted from the data analyzing section 8 is converted from an ultrasonic scan direction (vertical scan) in the ultrasonic transmitting/receiving operation into a horizontal scan similar to that used in a conventional television monitor by the DSC 10. A display control section 11 converts the ultrasonic image signals having the scan direction converted by the DSC 10 into video signals. The system control section 12 controls each section of the ultrasonic diagnostic apparatus.

The operation of the first embodiment of the present invention will be described below.

An ultrasonic-transmit pulse generated by the transmit-pulse generating section 14 is inputted to the delay control section 3. In order to arrange a transmit deflection angle, the delay control section 3 sets different delay times for each of the plurality of ultrasonic transducers of the ultrasonic probe 1, and outputs the delay times to the ultrasonic transmit section 2. The delay times can be set by using the data stored in the delay-data storing section in advance. This is done because, if respective delay values of the ultrasonic transducers are calculated on a case-by-case basis in case where the number of the ultrasonic transducers mounted on the ultrasonic probe is increased, it takes too long time to set the delay times. Alternatively, if the setting time is in an acceptable range to diagnosis, the delay data may be set by the system control section 12 instead of using the delay data stored in the delay-data storing section 4.

The ultrasonic-transmit pulses are transmitted by the plurality of the ultrasonic transducers. The system control section 12 controls the ultrasonic transmitting section 2 to select desired ultrasonic transducers to be used for the ultrasonic transmit operation, from the plurality of ultrasonic transducers.

The ultrasonic transmission pulses are amplified by the ultrasonic transmitting section 2 and transmitted into the living body through the ultrasonic probe 1. The ultrasonic-transmit pulses transmitted to the living body are reflected by the living body tissue, and received by the ultrasonic probe 1 as the ultrasonic reflected waves. The ultrasonic reflected waves are then converted into electric signals. The ultrasonic reflected waves converted into the electric signals are processed, such as amplified, at the ultrasonic transmitting/receiving section, and then outputted to the phase detecting section 5 as the ultrasonic received signal. Each of the ultrasonic received signals inputted to the phase detecting section 5 is divided into a real-part signal and an imaginary-part signal through a so-called orthogonal detection, and outputted to the phase-difference detecting section 6.

Figure 2:
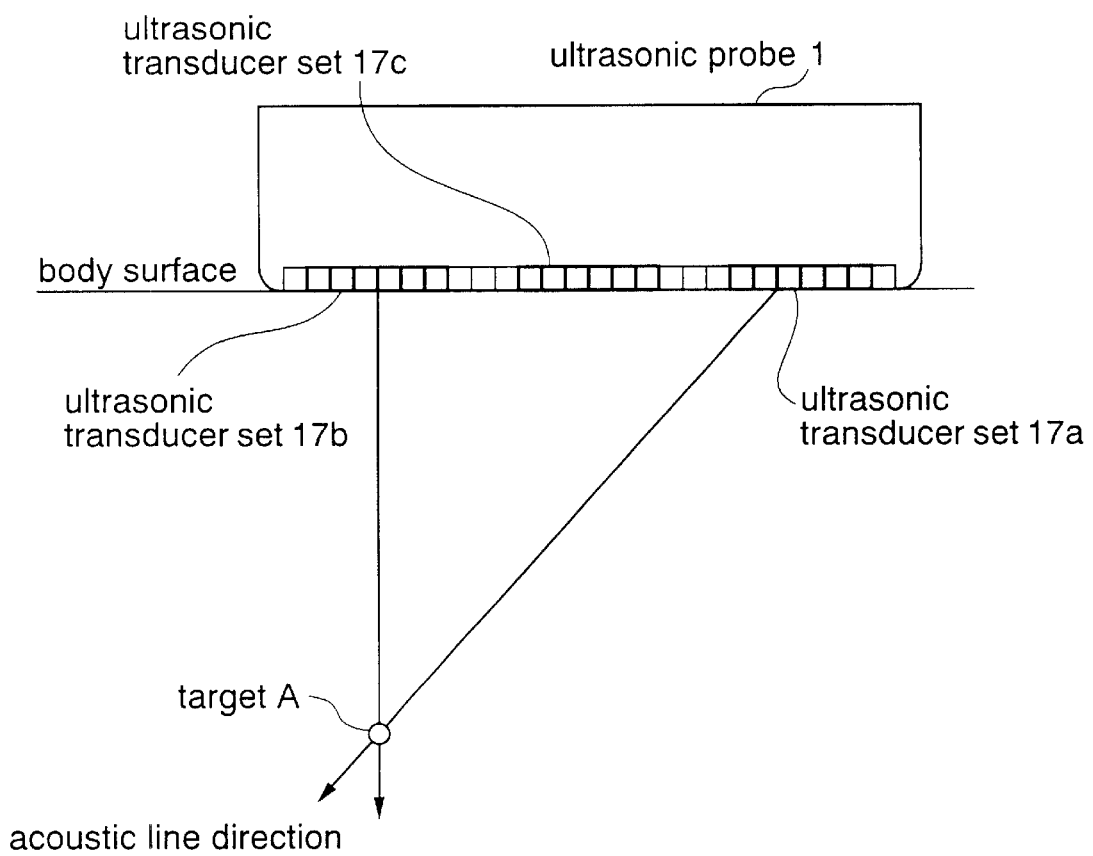
FIG. 2 is an explanatory diagram of the deflection of an acoustic line in the first embodiment of the present invention.

With reference to FIG. 2, the process in the phase-difference detecting section 6 of detecting phase-difference between the plurality of ultrasonic received signals received at the predetermined intervals will be described below.

Among the plurality of ultrasonic transducers of the ultrasonic probe 1, a given number of ultrasonic transducers are selected as a set to form an ultrasonic transducer set 17a. Based on the ultrasonic transducer set 17a, the process of detecting a phase-difference between the plurality of ultrasonic received signals received at the predetermined intervals from a target A will be described below.

Since the target A is not located directly below the ultrasonic transducer set 17a, an acoustic line defined by ultrasonic pulses transmitted and received by the ultrasonic transducer set 17a is required to be deflected. In the transmitting operation, the transducer closer to the center (closer to the target A) of the ultrasonic transducer set 17a is adapted to transmit the ultrasonic pulse having a longer delay time.

Thus, the ultrasonic pulses will be transmitted in turn from the out-side transducer of the ultrasonic transducer set 17a with given different delay times, and the ultrasonic pulses will be transmitted to the target A.

Each of the ultrasonic reflected waves reflected by the target A reaches the ultrasonic transducer set 17a after a certain time. However, the outermost transducer of the ultrasonic transducer set 17a receives the ultrasonic reflected wave lastly. Thus, the delay control section 3 carries out the receive processing for giving shorter delay time to the outer transducer of the ultrasonic transducer set 17a, so as to allow the ultrasonic reflected waves from the direction of the target A be received simultaneously by the ultrasonic transducer set 17a.

The ultrasonic transducer set 17a transmits ultrasonic pulses repetitively at predetermined intervals and carries out the receive processing repetitively during the time when the ultrasonic pulses are not transmitted. If the target A is not moving, the phases of the ultrasonic reflected waves repetitively received are the same every time, while, if the target A is moving, the received phases are changed due to the Doppler effect. In order to detect this phase difference, the phase data of the transmitted ultrasonic pulses is used as a reference phase data. In the repetitively received ultrasonic reflected waves, the phase data of the ultrasonic reflected waves preciously received are compared with the reference phase data, and the determined phase difference data are stored in the phase-difference data storing section 7. Then, the phase data of the currently received ultrasonic reflected wave are compared with the reference phase data, and the obtained phase difference data are compared with the previously received phase difference data stored in the phase-difference data storing section 7 to determine the phase difference.

In FIG. 2, the phase difference of the ultrasonic reflected waves due to the movement of the target A can also be detected by using an ultrasonic transducer set 17b located directly above the target A. In this case, the target A is located directly below the ultrasonic transducer set 17b, and thereby its acoustic line is not required to be deflected. Thus, no delay time control is necessary.

The movement velocity and displacement of the target A can be determined according to the following process of detecting a phase difference from different angles with respect to the target A by using a pair of ultrasonic transducer sets.

In order to determine the movement velocity of the target from the phase difference, the movement amount of the target is calculated from the phase difference between the phase of the previously received ultrasonic reflected wave and the phase of the currently received ultrasonic reflected wave, and from the wavelength of the ultrasonic waves. Then, the velocity of the target is calculated from the movement amount and the receive repetition-interval by using the following formula.

Velocity of Target=Movement Amount of Target A/Receive Repetition-Interval

Figure 3:
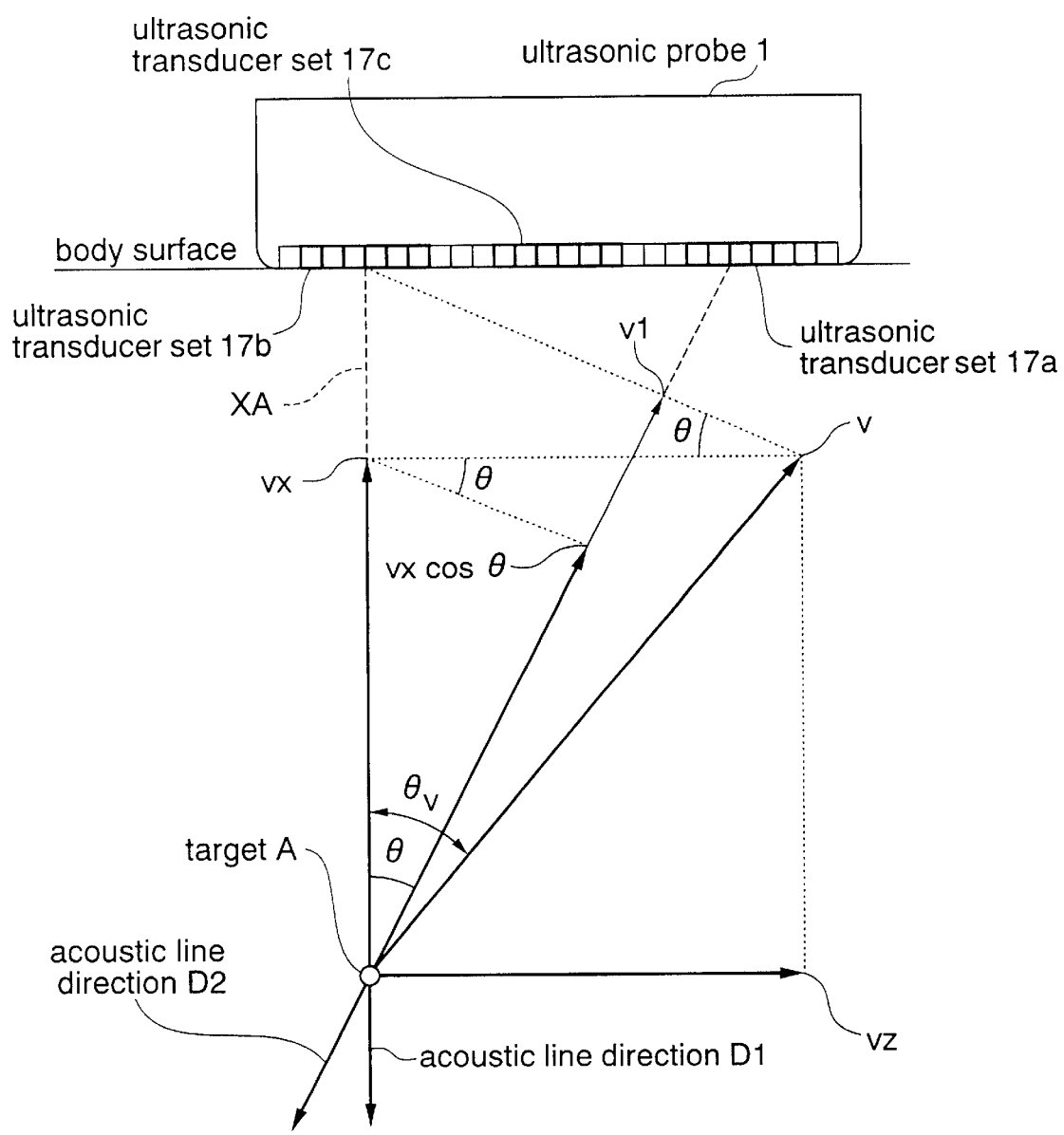
FIG. 3 is an explanatory diagram of a movement velocity measurement of a target by use of two kinds of acoustic line directions according to the first embodiment of the present invention.

Specifically, referring FIG. 3, the process for the data analyzing section 8 to determine the movement velocity and displacement of the target to be measured will be described. A target velocity v is the movement velocity of the target A to be measured. The x-direction component vx of the movement velocity is a velocity component of the target orthogonal to the surface of the ultrasonic probe 1, and the z-direction component vz of the movement velocity is a velocity component of the target parallel to the surface of the ultrasonic probe 1. The reference symbol vi is a velocity component of the movement velocity of the target in the direction from the ultrasonic transducer set 17a to the target A. The reference symbol θ is an angle between the direction from the ultrasonic transducer set 17a to the target A and the direction from the ultrasonic transducer set 17b to the target A.

When the target A is moving in a certain direction with respect to the surface of the ultrasonic probe 1, the movement velocity of the target A has the component vx in the acoustic line direction D1 and the component v1 in the acoustic line direction D2. When the component v1 in the acoustic line direction D2 is projected in the acoustic line direction D1 (hereinafter referred to as "x-axis-direction"), the following formula is satisfied;

$$vx + XA = v1/\cos\theta$$

where XA is a value arising from a component parallel to the surface of the ultrasonic probe 1 (hereinafter referred to as "z-axis-direction") included in the movement velocity of the target to be measured. Thus, if the z-axis direction component is not included in the movement velocity of the target to be measured, then XA=0.

The angle between the z-axis-direction component v1 of the target and XA is a deflection angle θ of the acoustic line direction D2, and therefore the z-axis-direction component vz can be is determined by the following formula (1).

$$vz = \frac{1}{\sin\theta}(v1 - vx\cos\theta) \qquad (1)$$

The movement velocity vx in x-axis-direction of the target is measured in the acoustic line direction D1. Thus, the velocity v of the target can be determined from the movement velocity vz in z-axis-direction and the movement velocity vx in x-axis-direction of the target by using the following formula (2).

$$V = \sqrt{VX^2 + VZ^2} \qquad (2)$$

Further, an angle θ v of the movement direction of the target with respect to the surface of the ultrasonic probe 1 can be determined by using the following formula (3)

$$\theta v = \tan^{-1}(vz/vx) \qquad (3)$$

In this manner, the movement velocity and displacement of the target to be measured can be calculated according to the determined x-axis-direction and z-axis-direction components of the movement velocity.

Further, the movement velocity is calculated according to phase differences in a plurality of acoustic line directions having different deflection angles, and then the moving velocities and displacements in both directions orthogonal to and parallel to the surface of the ultrasonic probe can be converted to polar coordinate system to detect velocity value and angle.

The information related to the movement velocity and displacement of the target calculated by the data analyzing section 8 is outputted to the DSC 10. In the DSC 10, the information related to the movement velocity and displacement is synthesized with a B-mode image and an M-mode image, and the scan direction thereof is converted so as to display it on the display section 13. The display control section 11 is adapted to display the B-mode image, the M-mode image, the information related to the movement velocity and displacement and others on the display section 13.

As described above, according to the first embodiment of the present invention, the ultrasonic pulses are transmitted to and received from the same target in a plurality of acoustic line directions having different deflection angles. Then, an arbitrary two-dimensional measurement region is selected on the B-mode image and M-mode image according to the information of the reflected waves received from the living body, and the phase-difference of the ultrasonic reflected waves from the living body in the selected region is determined. Thus, the movement velocity and displacement of the target can be calculated without complicated transmitting/receiving control based on the FFT Doppler method, FFT operation or the like.

A second embodiment of the present invention will be described below.

Figure 4:
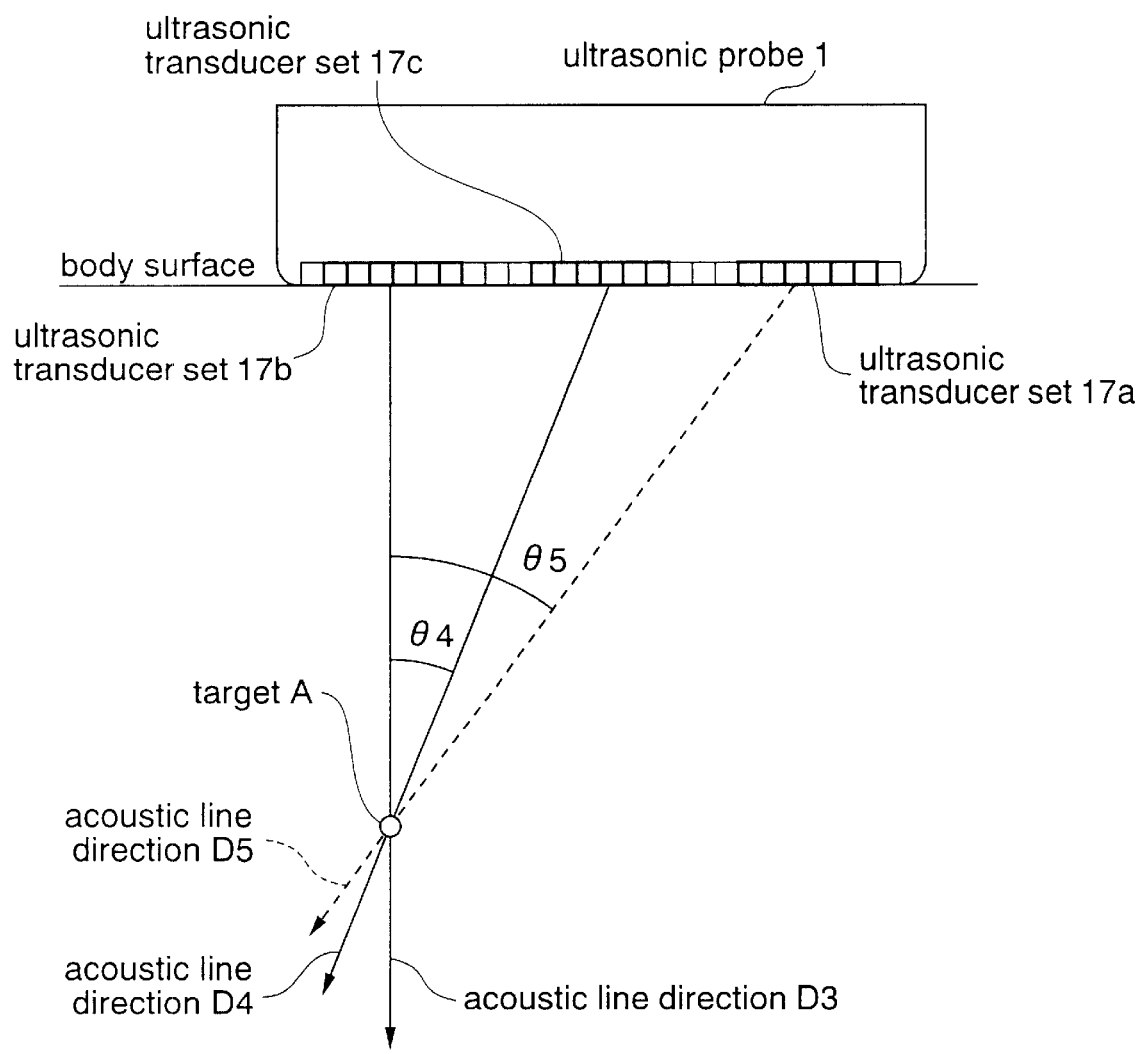
FIG. 4 is an explanatory diagram of a deflection angle control of each direction of acoustic lines from a plurality of ultrasonic transducer sets according to a second embodiment of the present invention.

Referring to FIG. 4, in an ultrasonic diagnostic apparatus according to the second embodiment of the present invention, the process of calculating the movement velocity and displacement of the target to be measured according to a plurality of deflection angles will be described.

The second embodiment has the same construction as that employed in the first embodiment, and therefore the description of the construction will be omitted.

As shown in FIG. 4, three ultrasonic transducer sets 17a, 17b, 17c are used to calculate the movement velocity and displacement of the target A according to a plurality of deflection angles. The ultrasonic transducer set 17b is located directly above the target A, and the ultrasonic transducer set 17a is located at a farthermost position from the target A. The ultrasonic transducer set 17c is located between the ultrasonic transducer set 17a and the ultrasonic transducer set 17b.

No delay control is necessary for the ultrasonic transducer set 17b because it is located directly above the target A. The ultrasonic transducer set 17a is located at an angle θ5 with the target A (in the direction of the acoustic line direction D5). Thus, the delay control section 3 controllably provides a delay time corresponding to the angle θ5 to the ultrasonic transducer set 17a. Further, the ultrasonic transducer set 17c is located at the angle θ4 with the target A (in the direction of the acoustic line direction D4). Thus, the delay control section 3 controllably provides a delay time corresponding to the deflection angle θ4 to the ultrasonic transducer set 17a.

As stated above, according to the second embodiment of the present invention, each phase-difference in the deflection angles θ4 and θ5 is detected, and the detected phase-differences are averaged to provide enhanced accuracy of the phase difference detection. This process is effective in case where the target A has a small component of the movement velocity parallel to the surface of the ultrasonic probe 1 or the target A is located close to the surface of the ultrasonic probe 1.

A third embodiment of the present invention will be described below.

Figure 5:
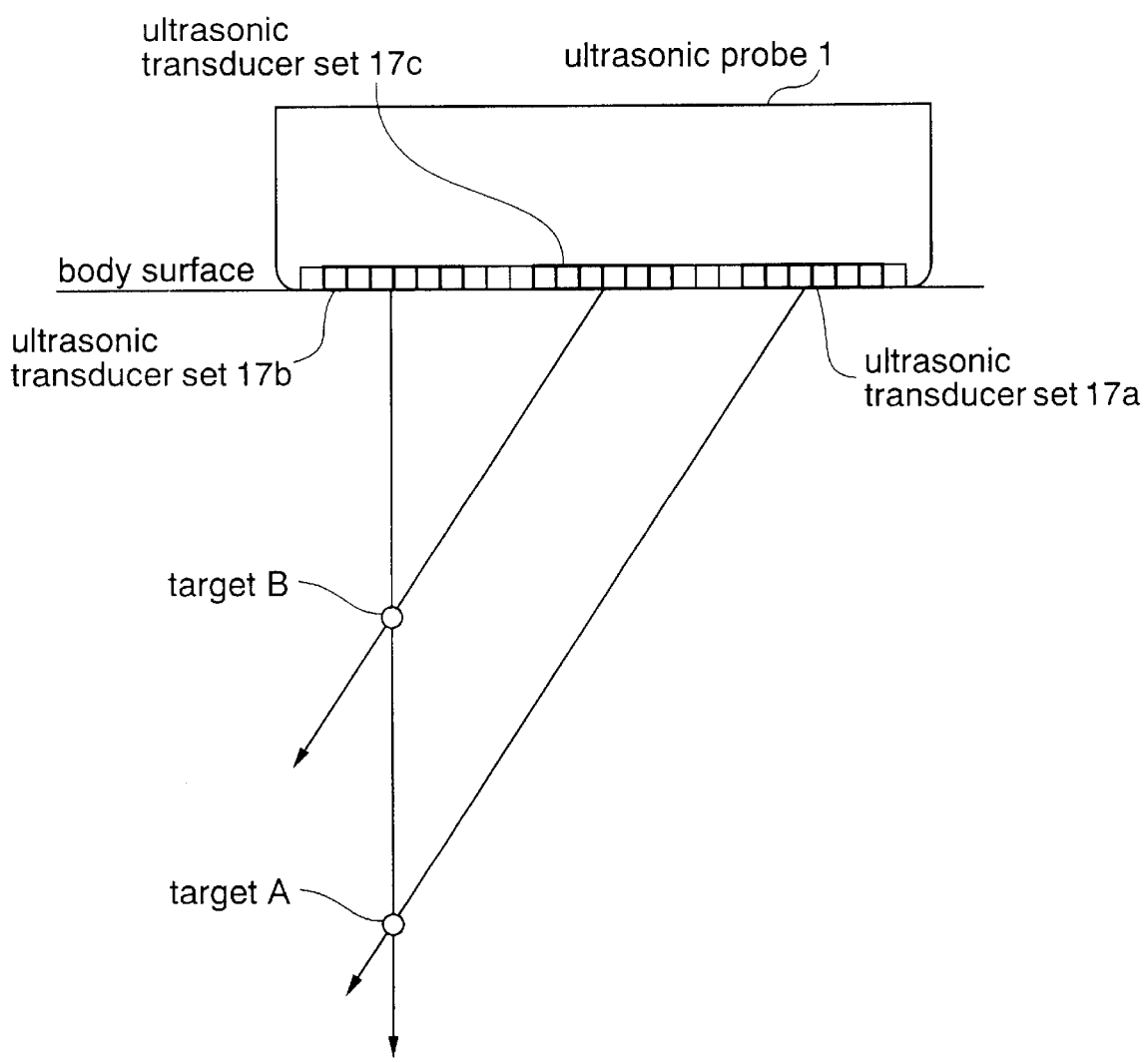
FIG. 5 is an explanatory diagram of a movement velocity measurement of a plurality of targets to be measured according to a third embodiment of the present invention.
Figure 6:
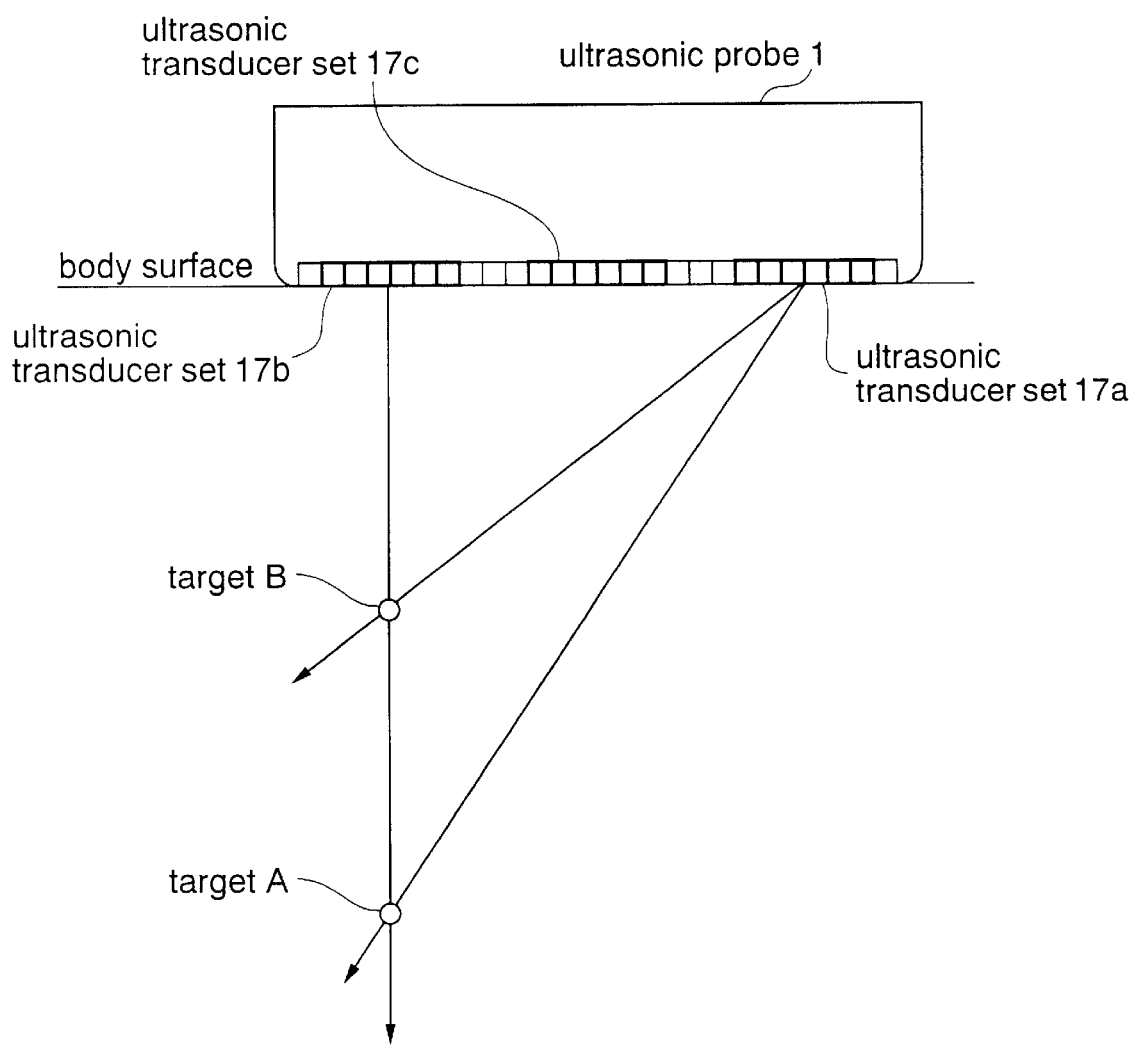
FIG. 6 is an explanatory diagram of a movement velocity measurement of a plurality of targets to be measured according to the third embodiment of the present invention.

Referring to FIGS. 5 and 6, in an ultrasonic diagnostic apparatus according to the third embodiment of the present invention, the process of determining the movement velocity and displacement of each of targets to be measured located at different positions will be described.

The third embodiment has the same construction as that of the first embodiment described in conjunction with FIG. 1, and therefore the description of the construction will be omitted.

As shown in FIG. 5, three ultrasonic transducer sets 17a, 17b, 17c are used to calculate the movement velocity and displacement of each of a plurality of targets A and B located at different positions. As in the process described in FIG. 2, a phase difference of the ultrasonic received signals received, respectively, by the ultrasonic transducer set 17a and the ultrasonic transducer set 17b is detected to calculate the movement velocity of the target A.

On the other hand, the ultrasonic transducer set 17b located directly above the target B and the ultrasonic transducer set 17c located closer to the center of the ultrasonic probe 1 than the ultrasonic transducer set 17a are used to calculate the movement velocity of the target B. For the ultrasonic transmitting/receiving operation in the ultrasonic transducer set 17c, the delay control section 3 may perform the same delay time control as that of the ultrasonic transducer 17a.

As stated above, the ultrasonic transducer set 17a and the ultrasonic transducer set 17b are used when calculating the movement velocity and displacement of the target A, and the ultrasonic transducer set 17a and the ultrasonic transducer set 17c are used when calculating the movement velocity and displacement of the target B. Thus, the moving velocity and the displacement of each of the targets located at different positions can be calculated simultaneously or almost simultaneously without changing the delay time.

Further, as shown in FIG. 6, when the movement velocity and displacement of the object B are calculated, the ultrasonic transducer set 17a can be used, and setting its deflection angle of the acoustic line larger. In this case, for controlling the delay time for the ultrasonic transducer set 17a, delay data for the target A as a target to be measured and delay data for target B may be stored in the delay data storing section 4. Thus, when the target to be measured is changed, the stored data can be read from the data storing section 4 to follow the changing of the target. This allows the movement velocity and displacement of each of the targets located at different positions to be calculated simultaneously or almost simultaneously.

Further, as shown in FIG. 7, when a plurality of targets to be measured are located at different positions in both vertical and horizontal directions, the moving velocity and displacement of each of the targets located at different positions can be calculated simultaneously or almost simultaneously by transmitting and receiving ultrasonic pulses which have different positions and deflection angles, respectively, to the ultrasonic transducer sets, as in the case described above.

While the target to be measured has been described as a point in the aforementioned embodiments of the present invention, the target to be measured is not limited to a point. For example, both of the B-mode and M-mode displays may be used, and any two-dimensional region in the B-mode and M-mode images may be designated to calculate the movement velocity and displacement of the designated region simultaneously or almost simultaneously.

A fourth embodiment of the present invention will be described below.

The fourth embodiment has the same construction as that of the first embodiment described in conjunction with FIG. 1, and therefore the description of the construction will be omitted.

When an ultrasonic diagnostic image is displayed on the display section 13, one image plane is typically displayed with a tomographic image composed of several hundreds of acoustic lines. This one image plane is referred to as a scan frame.

In the ultrasonic transmitting/receiving operation, a deflection angle in the acoustic line direction is arbitrarily set for each of the scan frames to detect a phase difference for each of the scan frames. Then, according to the same manner as that described in the first embodiment, the movement velocity and displacement of a target are calculated. An arbitrary two-dimensional measurement region can be selected according to information related to two-dimensional reflected waves from a received living body, and a phase difference of ultrasonic reflected waves of arbitrary different deflection angles for each of given scan frames from the living body associated with the selected region is determined simultaneously or almost simultaneously. Thus, a deflection angle in the optimum acoustic line direction for the position of the target can be set for each of the scan frames.

Accordingly, each of the scan frames can be displayed with giving priority to the B-mode display, and thereby the movement velocity and displacement of the target can be calculated without degrading the image quality of the B-mode image.

Further, a deflection angle of an acoustic line for each of the scan frames is controlled, and a phase difference between the different deflection angles is determined. Then, the phase-difference detecting section 6 or the data analyzing section 8 can select the phase-difference data between the deflection angles to provide the optimum movement velocity and displacement for each of the selected measurement regions. Thus, the movement velocity and displacement of the target can be determined with setting the deflection angle optimum all the time.

A fifth embodiment of the present invention will be described below.

An ultrasonic diagnostic apparatus according to the fifth embodiment of the present invention is adapted to allow a blood-pressure meter 15 and an electrocardiograph 16 to be connected therewith, and to allow a maximum blood pressure, a minimum blood pressure and an electrocardiographic waveform to be inputted thereto. This ultrasonic diagnostic apparatus comprises data analyzing means 8 for determining the movement velocity and displacement of an arterial wall and an intra-arterial blood flow for each heartbeat to determine a hysteresis curve between the movement velocity and displacement of the arterial wall and the velocity and displacement of the blood flow.

Two targets to be measured, one being an intra-arterial blood flow and the other being an arterial wall, are selected to calculate each movement velocity and displacement thereof. Further, the artery can be displayed by the M-mode with the electrocardiographic waveform on the display section 13. FIG. 8 shows an example of the electrocardiographic waveform and the M-mode display of the artery.

In FIG. 8, the electrocardiographic waveform 20 is inputted from the electrocardiograph 16. An R-wave 21 is a part of the electrocardiographic waveform, and appears when the heart discharges blood from a left ventricle to an aoarta. The displacement 22 of the arterial wall (anterior wall) represents a temporal variation of the displacement of the arterial wall closer to the skin. The displacement 23 of the intra-arterial cavity represents a temporal variation of the displacement of the intra-arterial cavity. The displacement 24 of the arterial wall (posterior wall) represents a temporal variation of the displacement of the arterial wall farther from the skin.

The heart is contracted at the timing t0 of the R-wave 21 to discharge the blood to the artery. The displacement 22 of the arterial wall (anterior wall) and the displacement 24 of the arterial wall (posterior wall) show that a pressure wave of blood (hereinafter referred to as "pulse wave") caused by the heart contraction is propagated to the artery after the time "t" elapsed from t0 to provide an expansion of the artery and a variation in thickness of the arterial wall. The time "t" can be set arbitrarily. While the R-wave of the electrocardiographic waveform is used in the above example, any other suitable waves, such as Q-wave or S-wave, can be used.

Figure 9:
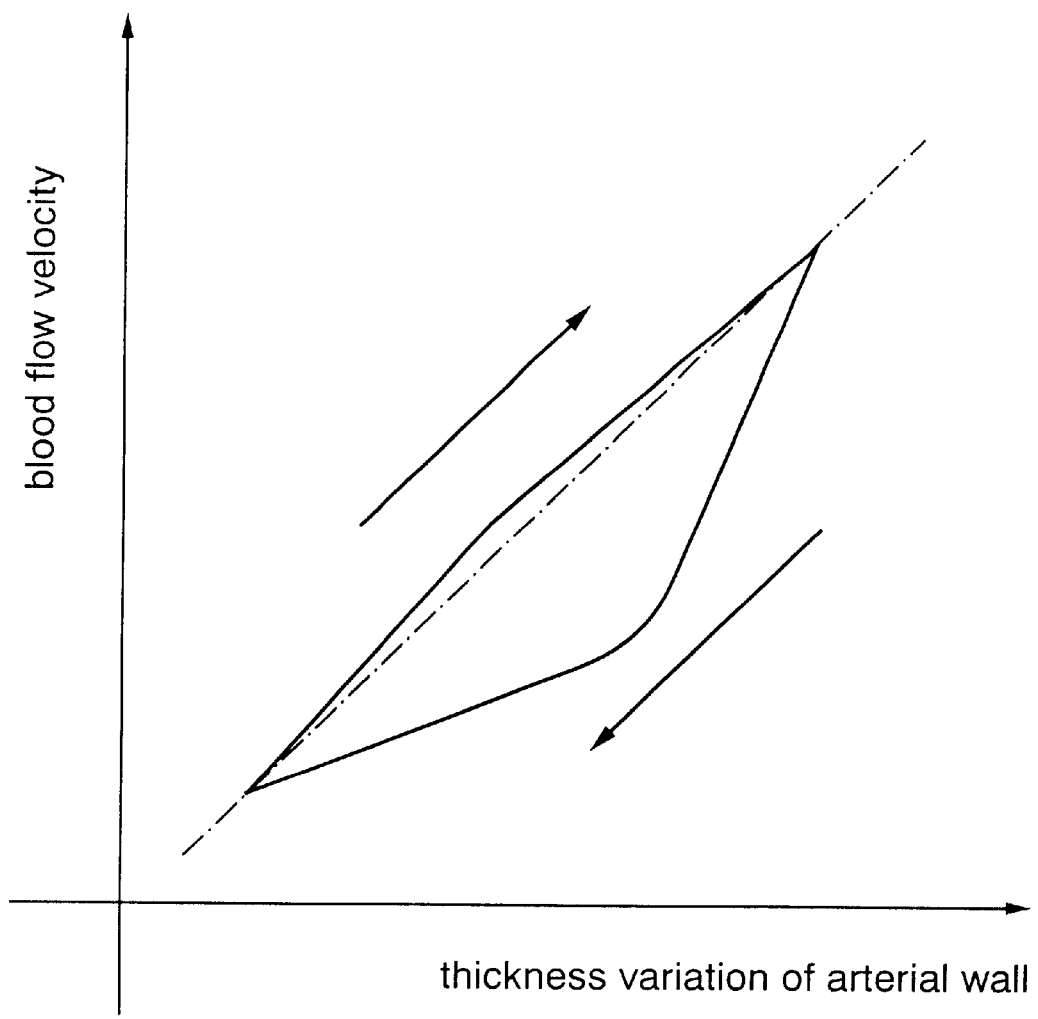
FIG. 9 illustrates the relationship between the displacement of the arterial wall and a blood flow velocity according to the fifth embodiment of the present invention.

Further, the velocity data of the intra-arterial blood flow and the displacement data of the arterial wall at the time "t" are calculated, and these calculated date are stored in the calculated data storing section 9 for each of the ultrasonic received signals. Then, the data analyzing section 8 can analyze these data to allow the analyzed variation to be displayed on the display section 13 as a graph. The graph is shown in FIG. 9. The horizontal axis is the thickness variation of the arterial wall and the vertical axis is the velocity of the intra-arterial blood flow.

Generally, when atherosclerosis is developed, the arterial wall becomes hard and thereby the thickness variation of the arterial wall caused by the propagation of the pulse waves becomes lower. Thus, the relationship between the blood flow velocity and the thickness variation of the arterial wall is shown in FIG. 9. As the arterial wall becomes harder due to the progress of atherosclerosis, the graph has larger gradient. This provides a significantly effective indicator of atherosclerosis. The arterial wall exhibits a hysteresis curve as shown in FIG. 9 because of its viscosity in addition to elasticity.

As stated above, according to the fifth embodiment of the present invention, the M-mode image of the arterial wall can be displayed in conjunction with the electrocardiographic waveform, and the relationship between the blood velocity and the thickness variation of the arterial wall can be graphed out at any timing of the electrocardiographic waveform. This provides enhanced accuracy in the atherosclerosis diagnosis.

Further, the velocity of the intra-arterial blood flow is normalized according to the maximum and minimum blood pressures inputted from the external blood-pressure meter, and the velocity of the intra-arterial blood flow is converted into the blood pressure. Thus, the relationship between the thickness variation of the arterial wall and the blood pressure variation can be graphed out.

As described above, according to the present invention, ultrasonic pulses are transmitted to and received from the same target in the plurality of acoustic line directions having different deflection angles, and respective phases of the ultrasonic reflected waves are detected to determine a phase difference between a plurality of continuous phase signals in the detected phase signals. Then, according to the phase difference, the movement velocity and displacement of the living body tissue can be calculated, and the movement of the living body tissue and the blood flow variation can be measured simultaneously. Because of this construction, it is easy to determine the relationship between the blood variation and the movement of the arterial wall. Thus, the present invention can provide an ultrasonic diagnostic apparatus having an effect of enhancing accuracy in diagnosis of a lesion, particular in the circulatory system.

What is claimed is:

1. An ultrasonic diagnostic apparatus comprising:

an ultrasonic transmitting/receiving means having an ultrasonic probe including a plurality of ultrasonic transducers, said ultrasonic transmitting/receiving means being operable to transmit ultrasonic pulses into a living body and to receive ultrasonic reflected waves reflected by tissue in the living body via said ultrasonic probe;

a phase detecting means operable to detect a phase of each ultrasonic reflected wave received by said ultrasonic transmitting/receiving means;

a phase-difference detecting means operable to detect a phase-difference between a plurality of phase signals detected at a predetermined time-interval by said phase detecting means;

a data analyzing means operable to analyze a movement of tissue including blood flow in the living body based on the detected phase-difference;

a display means operable to display the movement of the tissue;

a delay control means operable to control a delay value of each of the ultrasonic pulses and ultrasonic reflected waves which are transmitted and received by each of said plurality of ultrasonic transducers to control a deflection angle of acoustic lines defined by the ultrasonic pulses and the ultrasonic reflected waves; and a blood-pressure input means for inputting a signal from a blood-pressure meter, wherein said phase detecting means is further operable to detect the phase-difference for each of the plurality of acoustic lines having different deflection angles, wherein said data analyzing means is further operable to calculate a velocity and displacement of the tissue according to the phase-difference for each of the plurality of acoustic lines, and wherein said data analyzing means is further operable to normalize a displacement of an intra-arterial blood flow with a maximum blood pressure and a minimum blood pressure entered from the blood-pressure meter to convert the displacement into a blood pressure variation so as to allow said display means to display a graph representing the relationship between the velocity or displacement of the arterial wall and the blood pressure variation.

2. An ultrasonic diagnostic apparatus as defined in claim 1, wherein said data analyzing means is further operable to detect the orthogonal and parallel components of the velocity of the tissue according to the phase-difference for each of the plurality of acoustic lines, and to calculate the velocity and displacement of the tissue based on the detected orthogonal and parallel components of the velocity, and wherein the orthogonal and parallel components are orthogonal to and parallel to the surface of said ultrasonic probe, respectively.

3. An ultrasonic diagnostic apparatus as defined in claim 2, further comprises a transducer selecting means operable to select said plurality of ultrasonic transducers, to form a plurality of ultrasonic transducer sets, each composed of a given number of adjacent ultrasonic transducers selected from said plurality of ultrasonic transducers, and to select a plurality of said ultrasonic transducer sets, and wherein said data analyzing means is further operable to calculate the velocity and displacement of the tissue based on the phase-difference for each of the acoustic lines of the selected ultrasonic transducer sets.

4. An ultrasonic diagnostic apparatus as defined in claim 2, further comprising:

a diagnostic-image construction means for constructing an ultrasonic diagnostic image according to information related to said ultrasonic reflected waves, wherein at least one measurement region can be selected from the ultrasonic diagnostic image having a plurality of measurement regions and constructed by said diagnostic image construction means, and wherein said phase-difference detecting means or is further operable to detect the phase-difference of the ultrasonic reflected waves associated with said at least one selected measurement region simultaneously or almost simultaneously to allow said data analyzing means to calculate the velocity and displacement of the tissue in the selected measurement region.

5. An ultrasonic diagnostic apparatus as defined in claim 2, further comprising means for converting the movement velocity and displacement of the tissue to a polar coordinate system to determine a velocity value and angle.

6. An ultrasonic diagnostic apparatus as defined in claim 2, further comprising electrocardiographic-signal input means for inputting a signal from an electrocardiograph, and the displaying means display an image wherein said input electrocardiographic signal and the displacement of an arterial wall are related to each other.

7. An ultrasonic diagnostic apparatus as defined in claim 1, further comprises a transducer selecting means operable to select said plurality of ultrasonic transducers, to form a plurality of ultrasonic transducer sets, each composed of a given number of adjacent ultrasonic transducers selected from said plurality of ultrasonic transducers, and to select a plurality of said ultrasonic transducer sets, and wherein said data analyzing means is further operable to calculate the velocity and displacement of the tissue based on the phase-difference for each of the acoustic lines of the selected ultrasonic transducer sets.

8. An ultrasonic diagnostic apparatus as defined in claim 7, wherein said delay control means is further operable to arbitrarily control each deflection angle of the acoustic lines of said ultrasonic transducer sets, and wherein said data analyzing means is further operable to calculate the velocity and displacement of the tissue based on the phase difference for each of the acoustic lines.

9. An ultrasonic diagnostic apparatus as defined in claim 8, further comprising:

a diagnostic-image construction means for constructing an ultrasonic diagnostic image according to information related to said ultrasonic reflected waves, wherein at least one measurement region can be selected from the ultrasonic diagnostic image having a plurality of measurement regions and constructed by said diagnostic image construction means, and wherein said phase-difference detecting means or is further operable to detect the phase-difference of the ultrasonic reflected waves associated with said at least one selected measurement region, simultaneously or almost simultaneously, to allow said data analyzing means to calculate the velocity and displacement of the tissue in the selected measurement region.

10. An ultrasonic diagnostic apparatus as defined in claim 8, further comprising means for converting the movement velocity and displacement of the tissue to a polar coordinate system to determine a velocity value and angle.

11. An ultrasonic diagnostic apparatus as defined in claim 8, further comprising electrocardiographic-signal input means for inputting a signal from an electrocardiograph, and wherein said displaying means is further operable to display an image such that the input electrocardiographic signal and the displacement of an arterial wall are related to each other.

12. An ultrasonic diagnostic apparatus as defined in claim 7, further comprising:

a diagnostic-image construction means for constructing an ultrasonic diagnostic image according to information related to said ultrasonic reflected waves, wherein at least one measurement region can be selected from the ultrasonic diagnostic image having a plurality of measurement regions and constructed by said diagnostic image construction means, and wherein said phase-difference detecting means is further operable to detect the phase-difference of the ultrasonic reflected waves associated with said at least one selected measurement region, simultaneously or almost simultaneously, to allow said data analyzing means to calculate the velocity and displacement of the object in the selected measurement region.

13. An ultrasonic diagnostic apparatus as defined in claim 7, further comprising means for converting the velocity and displacement of the tissue to a polar coordinate system to determine a velocity value and angle.

14. An ultrasonic diagnostic apparatus as defined in claim 7, further comprising electrocardiographic-signal input means for inputting a signal from an electrocardiograph, and wherein said displaying means is further operable to display an image such that the input electrocardiographic signal and the displacement of an arterial wall are related to each other.

15. An ultrasonic diagnostic apparatus as defined in claim 1, further comprising:

a diagnostic-image construction means for constructing an ultrasonic diagnostic image according to information related to said ultrasonic reflected waves, wherein at least one measurement region can be selected from the ultrasonic diagnostic image having a plurality of measurement regions and constructed by said diagnostic image construction means, and wherein said phase-difference detecting means or is further operable to detect the phase-difference of the ultrasonic reflected waves associated with said at least one selected measurement region, simultaneously or almost simultaneously, to allow said data analyzing means to calculate the velocity and displacement of the tissue in the selected measurement region.

16. An ultrasonic diagnostic apparatus as defined in claim 15, wherein said delay control means is further operable to set each deflection angle of the acoustic lines for each of scan frames, and wherein said phase-difference detecting means is further operable to detect the phase-difference of the ultrasonic reflected waves for each of said scan frames having said arbitrarily-set deflection angles, simultaneously or almost simultaneously, in said at least one of selected measurement region.

17. An ultrasonic diagnostic apparatus as defined in claim 16, further comprising means for converting the velocity and displacement of the tissue to a polar coordinate system to determine a velocity value and angle.

18. An ultrasonic diagnostic apparatus as defined in claim 16, further comprising includes electrocardiographic-signal input means for inputting a signal from an electrocardiograph, and wherein said displaying means is further operable to display an image such that the input electrocardiographic signal and the displacement of an arterial wall are related to each other.

19. An ultrasonic diagnostic apparatus as defined in claim 15, further comprising means for converting the velocity and displacement of the tissue to a polar coordinate em to determine a velocity value and angle.

20. An ultrasonic diagnostic apparatus as defined in claim 15, further comprising electrocardiographic-signal input means for inputting a signal from an electrocardiograph, and wherein said displaying means is further operable to display an image such that the input electrocardiographic signal and the displacement of an arterial wall are related to each other.

21. An ultrasonic diagnostic apparatus as defined in claim 1, further comprising:
an electrocardiographic-signal input means for inputting a signal from an electrocardiograph,
wherein the displaying means is further operable to display an image such that the input electrocardiographic signal and the displacement of an arterial wall are related to each other, and
wherein said data analyzing means is further operable to calculate the velocity and displacement of each of an arterial wall and an intra-arterial blood flow, and to determine the relationship between the velocity or displacement of the arterial wall and the velocity or displacement of the intra-arterial blood flow so as to allow said display device to display a graph representing the relationship.

22. An ultrasonic diagnostic apparatus as defined in claim 21, wherein said data analyzing means is further operable to arbitrarily set a delay time from the time when an R-wave of the electrocardiographic signal is generated, and to calculate the velocity and displacement of each of an arterial wall and an intra-arterial blood flow at the set delay time so as to allow said display means to display a graph representing the relationship between the movement velocity or displacement of the arterial wall and the movement velocity or displacement of the intra-arterial blood flow.

23. An ultrasonic diagnostic apparatus as defined in claim 22, further comprising:
a blood-pressure input means for inputting a signal from a blood-pressure meter, wherein said data analyzing means is further operable to normalize a displacement of an intra-arterial blood flow with a maximum blood pressure and a minimum blood pressure entered from the blood-pressure meter to convert the displacement into a blood pressure variation so as to allow said display means to display a graph representing the relationship between the velocity or displacement of the arterial wall and the blood pressure variation.

24. An ultrasonic diagnostic apparatus comprising:
an ultrasonic transmitter/receiver having an ultrasonic probe including a plurality of ultrasonic transducers, said ultrasonic transmitter/receiver being operable to transmit ultrasonic pulses toward an object and to receive ultrasonic reflected waves reflected by the object via said ultrasonic probe;
a phase detector operable to detect a phase of each ultrasonic reflected wave received by said ultrasonic transmitter/receiver;
a phase-difference detector operable to detect a phase-difference between a plurality of phase signals detected at a predetermined time-interval by said phase detector;
a data analyzer operable to analyze a movement of at least a portion of the object based on the detected phase-difference;
a display device operable to display the movement of the at least a portion of the object;
a delay control device operable to control a delay value of each of the ultrasonic pulses and ultrasonic reflected waves which are transmitted and received by each of said plurality of ultrasonic transducers to control a deflection angle of acoustic lines defined by the ultrasonic pulses and the ultrasonic reflected waves; and
a blood-pressure input device operable to input a signal from a blood-pressure meter,
wherein said phase detector is further operable to detect the phase-difference for each of the plurality of acoustic lines having different deflection angles, and
wherein said data analyzer is further operable to calculate a velocity and displacement of the at least a portion of the object according to the phase-difference for each of the plurality of acoustic lines, and
wherein said data analyzer is further operable to normalize a displacement of an intra-arterial blood flow with a maximum blood pressure and a minimum blood pressure entered from the blood-pressure meter to convert the displacement into a blood pressure variation so as to allow said display device to display a graph representing the relationship between the velocity or displacement of the arterial wall and the blood pressure variation.

25. An ultrasonic diagnostic apparatus as defined in claim 24, wherein said data analyzer is further operable to detect the orthogonal and parallel components of the velocity of the at least a portion of the object according to the phase-difference for each of the plurality of acoustic lines, and to calculate the velocity and displacement of the at least a portion of the object based on the detected orthogonal and parallel components of the velocity, and
wherein the orthogonal and parallel components are orthogonal to and parallel to the surface of said ultrasonic probe, respectively.

26. An ultrasonic diagnostic apparatus as defined in claim 24, further comprises a transducer selector operable to select said plurality of ultrasonic transducers, to form a plurality of ultrasonic transducer sets, each composed of a given number of adjacent ultrasonic transducers selected from said plurality of ultrasonic transducers, and to select a plurality of said ultrasonic transducer sets, and
wherein said data analyzer is further operable to calculate the velocity and displacement of the at least a portion of the object based on the phase-difference for each of the acoustic lines of the selected ultrasonic transducer sets.

27. An ultrasonic diagnostic apparatus as defined in claim 24, further comprising:
a diagnostic-image constructor for constructing an ultrasonic diagnostic image according to information related to said ultrasonic reflected waves,
wherein at least one measurement region can be selected from the ultrasonic diagnostic image having a plurality of measurement regions and constructed by said diagnostic image constructor, and
wherein said phase-difference detector or is further operable to detect the phase-difference of the ultrasonic reflected waves associated with said at least one selected measurement region simultaneously or almost simultaneously to allow said data analyzer to calculate the velocity and displacement of the at least a portion of the object in the selected measurement region.

* * * * *